US005851816A

United States Patent [19]
Goodwin et al.

[11] Patent Number: 5,851,816
[45] Date of Patent: *Dec. 22, 1998

[54] CULTURED HIGH-FIDELITY THREE-DIMENSIONAL HUMAN UROGENITAL TRACT CARCINOMAS AND PROCESS

[75] Inventors: Thomas J. Goodwin; Tacey L. Prewett, both of Friendswood; Glenn F. Spaulding; David A. Wolf, both of Houston, all of Tex.

[73] Assignee: The United States of America as represented by the Administrator of the National Aeronautics and Space Administration, Washington, D.C.

[*] Notice: The portion of the term of this patent subsequent to Oct. 6, 2009, has been disclaimed.

[21] Appl. No.: 172,962

[22] Filed: Dec. 27, 1993

Related U.S. Application Data

[63] Continuation-in-part of Ser. No. 939,791, Sep. 3, 1992, Pat. No. 5,308,764, which is a continuation of Ser. No. 317,931, Mar. 2, 1989, Pat. No. 5,153,132, which is a continuation-in-part of Ser. No. 317,776, Mar. 2, 1989, Pat. No. 5,155,034, which is a continuation-in-part of Ser. No. 213,558, Jun. 30, 1988, Pat. No. 5,026,650, Ser. No. 213,559, Jun. 30, 1988, Pat. No. 4,988,623, and Ser. No. 625,345, Dec. 1, 1990, Pat. No. 5,153,131.

[51] Int. Cl.$^6$ ............................... C12N 5/02; C12N 5/06; A01N 1/02
[52] U.S. Cl. ................. 435/240.2; 465/240.23; 465/240.24; 465/240.25; 465/240.31
[58] Field of Search ............................ 435/240.2, 240.23, 435/240.24, 240.25, 240.31

[56] References Cited

U.S. PATENT DOCUMENTS

| | | | |
|---|---|---|---|
| 3,883,393 | 5/1975 | Knazek et al. | 435/240.242 |
| 4,220,725 | 9/1980 | Knazek et al. | 435/285 |
| 4,352,887 | 10/1982 | Reid et al. | 435/240.2 |
| 4,758,513 | 7/1988 | Takano et al. | 435/68 |
| 4,940,853 | 7/1990 | Vandenburgh | 435/240.23 |
| 4,962,033 | 10/1990 | Serkes et al. | 435/240.243 |
| 4,963,489 | 10/1990 | Naughton et al. | 435/240.1 |
| 4,988,623 | 1/1991 | Schwarz et al. | 435/286 |
| 5,026,650 | 6/1991 | Schwary et al. | 435/286 |
| 5,032,508 | 7/1991 | Naughton et al. | 435/32 |
| 5,153,131 | 10/1992 | Wolf et al. | 435/240.24 |
| 5,153,132 | 10/1992 | Goodwin et al. | 435/240.24 |
| 5,155,034 | 10/1992 | Wolf et al. | 435/240.24 |

OTHER PUBLICATIONS

Goodwin et al. In Vitro Cell Dev. Bio. 28A (pp. 47–60) Jan. 1992.
Kabalin et al. The Prostate, 14:251–263 (1989).
Sutterland et al. Science, vol. 240:177–184 (1988).
Buset et al, In Vitro Cell Dev. Bio 23(6):403–412 (Jun. 1987).
Shamsuddin, Colon Cancer Cells, Chapt. 6 pp. 137–153 (1990).
"Cell and Environment Interactions in Tumor Microregions:The Multicell Spheroid Model," Robert M. Sutherland, 240 Science 177–184 (Apr. 8, 1988).
"Development of Tissue Culture Procedures for Predicting the Indivdual Risk of Recurrence in Bladder Cancer", Joseph Leighton et al. 37 Cancer Research, 2854–2859 (Aug. 1977).
"Clinical Bladder Cancer in Sponge Matrix Tissue Culture–Procedures for Collection, cultivation, and Assessment of Viability,"Nabil A, Abaza et al, 42 Cancer 1364–74 (Sep. 1978).
"Sensitivities of Monolayers and Spheroids of the Human Bladder Cancer Cell Line MGH–UI to the Drugs Used for Intravesical Chemotherapy," Ruth Knuchel et al. 49 Cancer Research 1397 1401 (Mar. 15, 189).

*Primary Examiner*—Michael G. Witshyn
*Assistant Examiner*—Blaine Lankford
*Attorney, Agent, or Firm*—James M. Cate

[57] ABSTRACT

Artificial high-fidelity three-dimensional human urogenital tract carcinomas are propagated under in vitro-microgravity conditions from carcinoma cells. Artificial high-fidelity three-dimensional human urogenital tract carcinomas are also propagated from a coculture of normal urogenital tract cells inoculated with carcinoma cells. The microgravity culture conditions may be microgravity or simulated microgravity created in a horizontal rotating wall culture vessel.

25 Claims, 3 Drawing Sheets

CULTURED HIGH-FIDELITY THREE-DIMENSIONAL HUMAN UROGENITAL TRACT CARCINOMAS AND PROCESS

RELATED PATENTS AND APPLICATIONS

The present case is a continuation-in-part of U.S. patent application Ser. No. 07/939,791, filed Sep. 3, 1992, entitled "Three-Dimensional Coculture Process", now U.S. Pat. No. 5,308,764, issued May 3, 1994, which is a continuation of Ser. No. 07/317,931, filed Mar. 2, 1989, entitled "Three-Dimensional Coculture Process", now U.S. Pat. No. 5,153,132, issued Oct. 6, 1992, which is a continuation-in-part of Ser. No. 317,776, filed Mar. 2, 1989, entitled "Three Dimensional Cell and Tissue Assembly Process", now U.S. Pat. No. 5,155,034, issued Oct. 13, 1992, which is a continuation-in-part of Ser. No. 213,558, filed Jun. 30, 1988, now U.S. Pat. No. 5,026,650, issued Jun. 25, 1991, entitled "Horizontally Rotated Cell Culture System with a Coaxial Tubular Oxygenator" and Ser. No. 213,559, filed Jun. 30, 1988, now U.S. Pat. No. 4,988,623, issued Jan. 29, 1991, entitled "Rotating Bio-Reactor Cell Culture Apparatus", and Ser. No. 625,345, filed Dec. 11, 1990, now U.S. Pat. No. 5,153,131, issued Oct. 6, 1992, entitled "High Aspect Reactor Vessel and Method of Use", all of which are specifically incorporated by reference as if fully set forth herein. U.S. patent application Ser. No. 08/066,292, entitled "Cultured Normal Mammalian Tissue and Process", filed May 25, 1993, is a related application, and is also incorporated by reference.

ORIGIN OF THE INVENTION

The invention described herein was made in the performance of work under a National Aeronautics and Space Administration (NASA) contract and is subject to the provisions of Section 305 of the National Aeronautics and Space Act of 1958, Public Law 85-568 (72 Stat. 435; 42 U.S.C. 2457).

FIELD OF THE INVENTION

The invention relates to the production of high-fidelity three-dimensional human urogenital tract carcinomas from a culture of carcinoma cells maintained in a fluid culture media contained in a microgravity vessel. High-fidelity three-dimensional human-urogenital tract carcinomas were also cultured from a coculture of normal cells inoculated with carcinoma cells in fluid media contained in a microgravity vessel.

BACKGROUND OF THE INVENTION

Cell culture processes have been developed for the growth of single cell bacteria, yeast and molds, which are resistant to environmental stresses or are encased within a tough cell wall. Mammalian cell culture, however, is much more complex because the cells are delicate and have complex nutrient and other environmental requirements for maintaining viability and cell growth.

Large scale culture of bacterial-type cells is highly developed, and such culture processes are less demanding and less difficult to cultivate than mammalian cell cultures. For example, bacterial cells can be grown in large volumes of liquid medium and can be vigorously agitated without any significant damage. Mammalian cells, however, cannot withstand excessive turbulent action without damage to the cells. Mammalian cell cultures also require complex nutrient media to support cell proliferation and growth. Additionally, mammalian cells frequently require that the cells attach themselves to some substrate surface to remain viable and to duplicate. The particular culture requirements of mammalian cells make successful in vitro culturing of both normal and neoplastic tumorous mammalian cells difficult.

Future successes in cancer therapy are dependent upon therapeutic testing in models that closely resemble tumorous tissue in situ. Although several human carcinoma cell lines have been propagated for many years, thereby allowing researchers to study and characterize various aspects of tumor genesis, present in vitro culture does not permit reproducible cultures of neoplastic cells in large-scale, three-dimensional configuration. The culture of most neoplastic cells has a low success rate, with low percentages of neoplastic cells being established in vitro.

Three-dimensional in vitro tumor models are intermediate in complexity between standard two-dimensional monolayer cultures in vitro and tumors in vivo. In vitro cultured three-dimensional tumors demonstrate overall growth characteristics similar to those of tumors in vivo. The techniques developed for producing in vitro three-dimensional tumor cell aggregates to mimic in vivo tumor cell growth, however, have been found to have many limiting aspects.

High-density, three-dimensional in vitro growth of mammalian tumor cells is problematic due to the effects of shear, turbulence, or inadequate oxygenation in conventional cell culture systems. On a small scale, mammalian tumor cells have been grown in containers with small microwells to provide surface anchors for the cells. However, cell culture processes for mammalian cells in such microwell containers generally do not provide sufficient surface area to grow mammalian cells on a sufficiently large scale basis for many commercial or research applications.

Adenocarcinomas and melanomas have been grown in culture systems to provide three-dimensional growth in the presence of a pre-established stromal support matrix. U.S. Pat. No. 4,963,489, Three-Dimensional Cell and Tissue Culture System, Naughton, et al., Oct. 16, 1990; U.S. Pat. No. 5,032,508, Three-Dimensional Cell and Tissue Culture System, Naughton, et al., Jul. 16, 1991. A biocompatible, non-living material formed into a three-dimensional structure is inoculated with stromal cells. In some cases, the three-dimensional structure is a mesh pre-coated with collagen. Stromal cells and the associated connective tissue proteins naturally secreted by the stromal cells attach to and envelop the three-dimensional structure. The interstitial spaces of the structure become bridged by the stromal cells, which are grown to at least subconfluence prior to inoculating the three-dimensional stromal matrix with tissue-specific cells.

Conventional culture processes have been utilized to produce limited size and viability tumor cell aggregates. The multicell tumor cell spheroids produced without attachment substrates have been used to study cell and environmental interactions in tumors. Sutherland, R. M., "Cell and Environmental Interactions in Tumor Microregions: The Multicell Spheroid Model", 240 *Science* 177–184 (Apr. 8, 1988). Such three-dimensional cell aggregates have been used for studies of regulation of embryological development in a variety of malignant cell types, including carcinomas.

Collagen-coated cellulose sponges have been used to study three-dimensional growth of bladder cancer cells in vitro. Leighton, J., et al., "Development of Tissue Culture Procedures for Predicting the Individual Risk of Recurrence in Bladder Cancer", 37 *Cancer Res.* 2854–59 (August 1977). The sponges allow carcinoma and other cancer-type cells to adhere, migrate, and proliferate on collagen substrates. Clinical tumor fragments are collected and a mince of tumor tissue placed in the sponge and the combination is embedded in a fibrin clot. The procedures for cultivating the carcinomas are complex and culture periods are limited due to degenerative changes which were found to begin to occur by the tenth day of culturing. Abaza, N. A., et al., "Clinical Bladder Cancer in Sponge Matrix Tissue Culture-Procedures for Collection Cultivation, and Assessment of Viability, 42 (3) Cancer 1364–74 (Sept. 1978).

Multicellular tumor spheroids of bladder cancer cell lines have been propagated using a microcarrier stirrer. Knuchel, R., et al., "Sensitivities of Monolayers and Spheroids of the Human Bladder Cancer Cell Line MGH-UI to the Drugs for Intravesical Chemotherapy", 49 Cancer Res. 1397–1401 (Mar. 15, 1989). The spheroids were initiated by inoculating a suspension of single cells into a medium-containing flask, and stirring the cells continuously over a predetermined period of time. The spheroids were grown to an average diameter of 0.7 mm, and used to study the cytotoxicities of drugs used for chemotherapy. Spheroids of larger sizes were not reported.

Microcarrier beads have been developed for providing increased surface areas for cultured cells to attach and to provide conditions which allow cells to assemble into tissues which simulate the spatial three-dimensional form of actual tissues in the intact organism. Microcarrier beads with attached cultured cells require agitation in a conventional bioreactor vessel to provide suspension of the cells, distribution of fresh nutrients, and removal of metabolic waste products. To obtain agitation, such bioreactor vessels have used internal propellers or movable mechanical agitation devices which are motor driven so that the moving parts within a vessel cause agitation in the fluid medium for the suspension of the microcarrier beads and attached cells. Agitation of mammalian cells, however, subjects them to high degrees of shear stress which can damage the cells and limit ordered assembly of these cells according to cell derived energy. These shear stresses arise when the fluid media has significant relative motion with respect to vessel walls, impellers, or other vessel components. Cells may also be damaged in bioreactor vessels with internal moving parts if the cells or beads with cells attached collide with one another or vessel components.

Coculture of tumor and normal cells in solid-state culture has been reported as shown in U.S. Pat. No. 4,352,887 to Reid et al., issued Oct. 5, 1982. However, the three-dimensional environment and culture did not achieve standard clinical testing protocol, such that the three-dimensional environment is nurtured by a mixed-bed of tumor and normal cells.

Three-dimensional tumor cell aggregates and growth provide a unique system in which to simulate the conditions of clinical therapy in vitro. The three-dimensional arrangement of cells in vitro can permit various combinations of physical, chemical, and nutritional stress factors to be tested under conditions that resemble those of in vivo tumors. In vitro screening of chemotherapeutic agents may utilize three-dimensional carcinoma cell aggregates to determine the potential effectiveness of particular therapies and to identify the optimal therapeutic regimen for an individual patient. Three-dimensional tumor models may also provide a means for early identification of patients who can expect serious recurrence and those who are unlikely to have recurrent disease.

Mammalian cell and tissue culture technology is essential to research concerning tumor genesis and tumor cell invasiveness. Therefore, it is important that tumor models utilized in vitro mimic to the extent possible, in vivo properties of tumor cell lines. Although animal models are useful for studying carcinomas, many biochemical and molecular studies require that cells be grown in vitro. Studies on carcinoma cell lines have centered around the expression of oncogenic and protooncogenic markers and nucleotide sequences in order to elucidate the etiology of malignant transformation. Studies have led to insight and speculation as to the origin of transformation, the genetics of transformation, and the treatment or inhibition of the transformation process. However, the models studied have lacked sufficient fidelity for adequate comparison of in vitro culture systems to observations in situ. In vitro tumor models have failed to provide intact cell sub-populations, stable isoenzyme patterns, stable ploidy, stable and broad-based growth patterns, and high-fidelity expression of specific cellular proteins. Large scale, high-fidelity three-dimensional in vitro culture carcinoma models are necessary to studying developmental, mutagenic, metastagenic and transformation properties of carcinomas.

SUMMARY OF THE INVENTION

Aggregates of human urogenital tract carcinoma cells have been cultured in vitro without the presence of normal cells. Human urogenital tract is defined herein to include the bladder, prostate, kidney and associated tissues emanating from common embryological origins. Urogenital tract carcinoma cells were introduced into a culture vessel containing culture media and culture matrix. The carcinoma cells were cultured at microgravity conditions, whereby the carcinoma cells formed cell aggregates. The microgravity conditions were maintained so that high-fidelity three-dimensional carcinoma growth was achieved from the monoculture.

Aggregates of human urogenital tract carcinoma cells were cocultured in vitro with normal mammalian cells. Normal mammalian cells were introduced into a culture vessel containing culture media and culture matrix. Urogenital tract carcinoma cells were added to the culture vessel and the microgravity culture conditions maintained so that the cocultured normal cells and carcinoma cells achieved high-fidelity three-dimensional carcinoma growth. The normal cells were cultured at microgravity conditions until the cells reproduced to form aggregates.

The aggregates were produced under "microgravity culture conditions" which can be microgravity or simulated microgravity. Simulated microgravity was created in unit gravity by modulating the horizontal rotation of a culture vessel completely filled with culture media containing a culture matrix with normal mammalian cells and urogenital tract carcinoma cells or only the carcinoma cells. In the preferred process, simulated microgravity was produced in a horizontally rotating wall culture vessel by the simultaneous conditions of (1) collocation of cells and culture matrix with similar or differing sedimentation properties in a similar spatial region, (2) freedom for three dimensional spatial orientation of cell aggregates formed by the culturing of the cells, and (3) low shear and essentially no relative motion of the culture environment with respect to the walls of the culture vessel. The culture conditions included mass transfer under microgravity conditions with exchange of nutrients for metabolic waste and appropriate gas exchange in the culture system.

The process for producing the urogenital tract carcinoma cell aggregates is particularly unique in that the resultant product is a cell aggregation of a size of 4 millimeters and larger. The size of the cell aggregations is significant because assembly of the three-dimensional masses of this size is not possible without the complex functional interrelationship of in situ urogenital tract carcinomas.

High-fidelity three-dimensional urogenital tract carcinomas were produced artificially by culturing urogenital tract carcinoma cells in a vessel containing culture media and a culture matrix, preferably of generally spherical microcarriers. The vessel is capable of culturing at microgravity culture conditions. The carcinoma cells were preferably dissociated prior to introduction into the culture vessel. Tissue engineering was employed by selectively introducing urogenital tract carcinoma cells and culture matrix into the vessel and then culturing the cells at microgravity culture conditions. The carcinoma cells were cultured under microgravity conditions whereby high-fidelity three-dimensional carcinoma growth was achieved.

The cultured and cocultured carcinoma cell aggregates exhibited three-dimensional growth, intact cell subpopulations of differentiated and undifferentiated cells, stable isoenzyme patterns, stable ploidy, stable and broad-based cell growth patterns and high-fidelity expression of specific cellular proteins, such as proteoglycan. Specific protein markers, such as Prostate Specific Antigen (PSA) and Prostatic Acid Phosphatase (PAP) were also expressed.

DETAILED DESCRIPTION OF THE INVENTION

Figure 1:
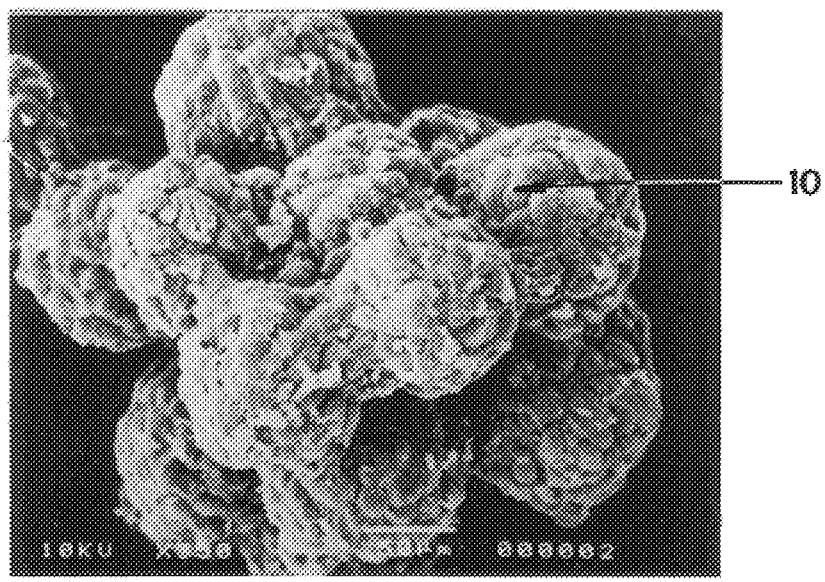
FIG. 1 is an SEM (scanning electron microscopy) at 91 hours of a cultured high-fidelity three-dimensional bladder carcinoma cell aggregation at 350× magnification.

Aggregates of human urogenital tract carcinoma cells were cultured in vitro to produce artificial high-fidelity three-dimensional carcinomas. The artificially-produced carcinoma masses exhibited intact cell subpopulations of differentiated and undifferentiated cells, stable isoenzyme patterns, stable ploidy, stable and broad-based cell growth patterns and high-fidelity expression of specific cellular proteins, specifically proteoglycan. Specific protein markers, such as Prostate Specific Antigen (PSA) and Prostatic Acid Phosphatase (PAP) were also expressed. Examples of human urogenital tract carcinomas cultured using the method of the present invention are described below.

Artificially-produced high-fidelity three-dimensional human prostate carcinomas were propagated from carcinoma cells obtained from a human prostate carcinoma. The prostate carcinoma cell lines propagated, designated PC3 and LnCap by convention, are primarily undifferentiated prostate carcinoma cell lines. Both prostate carcinoma cell lines are a mixed-bed carcinoma having a mixture of standard cell subpopulations. The carcinoma cell lines were obtained from American Type Culture Collection (ATCC, Rockville, Md.). The PC3 cells were ATCC no. CRL-1435 and the LnCap were ATCC no. CRL-1740. Both cell lines were successfully propagated according to the methods described herein. Carcinoma cells may also be obtained directly from the organ of carcinoma origin, or the organ of metastases.

In the preferred embodiment of the present invention, carcinoma cells were cocultured with normal human cells. The normal cells selected were normal adult prostate fibroblasts established from primary cultures from the normal prostate of organ donors. The normal fibroblasts were obtained from Clonetics Corporation (San Diego, Calif.). It is preferred that the fibroblasts selected be specific to the organ of interest.

The prostate carcinoma cells and the normal prostate fibroblasts were initiated and propagated separately in T-flasks containing a preferred culture media designated GTSF-2. A preferred formulation for GTSF-2 media is provided in Table 1 below.

The carcinoma cells and the fibroblasts were grown in monolayer culture. GTSF-2 was found to meet the growth requirements of the monolayer cultures, and the subsequent culture vessel system, without the need for unique growth factors and other complex components found in other media. The GTSF-2 media is a tri-sugar-based medium containing the sugars: glucose, galactose and fructose supplemented with 7% fetal bovine serum (FBS). The pH of the media was adjusted to 7.4 with 1N NaOH.

TABLE 1

| Tri-Sugar Based Medium GTSF-2 | | |
|---|---|---|
| Component | Concentration | Source/Order or Designation |
| MEM-alpha supplemented with 2.25 gm/L NaHCO$_3$ | 400 ml (40%) | GIBCO/410-1900EB |
| L-15 | 600 ml (60%) | GIBCO/430-1300EB |
| NaHCO$_3$ | 1.35 g/liter | Sigma/S-5761 |
| HEPES | 3. g/liter | Research Organics/6003H-2 |
| Folic acid | 6.667 µg/liter | Sigma/F-8758 |
| 0.05% Nicotinic acid | 0.667 ml/liter | Sigma/N-4126 |
| Bactopeptone | 0.6 g/liter | Difco/0118-01 |
| i-Inositol | 0.024 g/liter | Sigma/I-5125 |
| Fructose | 0.13 g/liter | Sigma/F-3510 |
| Galactose | 0.25 g/liter | Sigma/G-5388 |
| D-Glucose | 1.0 g/liter | Sigma/G-5250 |
| 300 mM L-Glutamine | 10 ml/liter | Sigma/G-5763 |
| Gentamycin | 1 ml/liter | GIBCO/600-5750AD |
| Fungizone | 2 ml/liter | GIBCO/600-5295AE |
| Insulin-transferrin-sodium-solenite | 5 ml/liter | Sigma/I-1884 |
| Fetal bovine serum | 70 ml (7%) | Hyclone/A-1111-L |

The monolayer cell cultures were maintained in a humidified $CO_2$ Forma incubator in 5% $CO_2$:95% air constant atmosphere, and 98% humidity at a temperature of 37° C. When glucose in the cell culture media was depleted to 20–60 mg/dl, 50 to 100% of the culture media was replaced. Cell cultures were expanded when cells became confluent on the bottom of the T-flasks. Standard enzymatic dissociation with a solution of 0.1% Trypsin, 0.1% EDTA, in phosphate-buffered saline (PBS) solution for 15 minutes at 37° C., was used to separate the cells.

Once the concentration of normal and carcinoma cells grown in monolayer culture was sufficient to provide the desired cell concentration for seeding into the culture vessel, the carcinoma cells and the normal fibroblasts were removed from the T-flasks. The cells were removed by enzymatic digestion with 0.1% Trypsin, 0.1% EDTA, for 15 minutes at 37° C., and washed once with calcium- and magnesium-free PBS (CMF-PBS). The cells were assayed for viability using Trypan Blue stain exclusion (GIBCO). The cells were centrifuged at 800×G for 10 minutes in conical 15-ml centrifuge tubes in GTSF-2 with 7% FBS. The cells were then resuspended in fresh medium and diluted into Corning T-flasks with 25 ml of fresh growth medium. Cells were held on ice in fresh growth medium until inoculation into a culturing vessel. The carcinoma cells and the normal fibroblasts cells were kept separate during preinoculation procedures.

In the preferred method, the primary inoculum of monodispersed normal cells introduced into the culture vessel was $4 \times 10^5$ normal prostate fibroblast cells/ml in the 110-ml volume vessel, with 5 mg/ml (550 mg total) Cytodex-3 microcarrier beads (Pharmacia, Piscataway, N.J.). Cytodex-3 microcarriers were Type I, collagen-coated dextran beads, 175 microns in diameter. After the primary inoculum was prepared for seeding, it was transferred to a culture vessel filled with GTSF-2 with 7% FBS culture media and cultured at microgravity conditions. Rotation speed in the vessel was initially set at a rate of 12–14 rpm.

In an alternate embodiment, a primary inoculum of the monodispersed prostate carcinoma cells was introduced into the culture vessel at $2 \times 10^5$ cells/ml in the 110 ml volume with 5 mg/ml Cytodex-3 micro-carrier beads, as described above for the preferred embodiment.

In yet another embodiment of the present invention, a primary inoculum of monodispersed normal cells may be introduced into the culture vessel at $4 \times 10^5$ normal prostate fibroblast cells/ml with an inoculum of $2 \times 10^5$ prostate carcinoma cells/ml with 5 mg/ml Cytodex-3 microcarrier beads described above. Thereby, a coculture of prostate carcinoma cells and normal prostate fibroblasts will be present in the vessel at the initiation of culturing.

The microgravity conditions were simulated in unit gravity by a horizontal rotating wall vessel (RWV) for both the preferred and alternate embodiments of the invention. A preferred horizontal rotating wall vessel (RWV) bioreactor is described in U.S. Pat. No. 5,153,131, Wolf et al., issued Oct. 6, 1992, and is incorporated by reference herein. The horizontally rotating wall vessel described in U.S. Pat. No. 5,026,650, Schwarz et al., issued Jun. 25, 1991, and incorporated herein by reference may also be used to culture high-fidelity three-dimensional urogenital tract carcinoma cells. The rotation of the culture vessel (bioreactor) was modulated to produce the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel.

The trajectory of the cell aggregates was determined during culturing. The speed of the rotation of the culture vessel was increased if the cell aggregates fell excessively inward and downward on the downward side of the rotational cycle and excessively outward and insufficiently upward on the upgoing side of the rotational cycle to prevent wall impact. The rotation of the culture vessel was decreased in response to excessive accumulation of tissue aggregation near the outer wall of the culture vessel so as not to restrict three dimensional growth. As the tissue aggregates grew, the rotation was adjusted to obtain minimal collision frequency and intensity.

Culture conditions included mass transfer with exchange of nutrients for metabolic waste and appropriate gas exchange in the culture system. The culture medium was changed in response to glucose depletion. Fresh medium was replenished by 50% of the total vessel volume each 20 to 24 hours.

Within 48 hours of inoculation, the preferred primary inoculum of monodispersed normal human prostate fibroblasts formed visible three-dimensional cellular aggregates. The fibroblast aggregates were maintained in solution through rotation of the RWV at 25 rpm. The fibroblasts were allowed to become confluent such that the beads were entirely covered before a coculture inoculum of $2 \times 10^5$ prostate carcinoma cells/ml was added to the culture vessel, resulting in a coculture of prostate carcinoma cells and normal cells. Although normal prostate fibroblasts were selected as the primary inoculum in the preferred embodiment, normal prostate mesenchymal cells, initiated and propagated as described herein for normal fibroblasts, may form the primary inoculum, inoculated at $4 \times 10^5$ normal mesenchyme cells/ml.

The coculture process described allows carcinoma tissues to be engineered, or constructed, through the control of culture conditions and the introduction of cells. Tissue engineering of carcinoma growth enables the manipulation of the results of the culture system by introducing various carcinoma cell types into the culture system at different points during the culturing process to obtain the desired cellular growth and aggregate size.

In an alternate embodiment, the monodispersed carcinoma cells formed visible cellular aggregates at approximately 72 hours post inoculation. The prostate cell aggregates were maintained through rotation of the RWV at 25 rpm. The prostate cell aggregates were maintained as a monoculture of prostate carcinoma cells. This culturing process also allows carcinoma tissues to be engineered, or constructed, through the control of culture conditions and the introduction of cells.

In the preferred embodiment and an alternate embodiment, cells were allowed to grow until the aggregates exceeded 4 mm in diameter (approximately 11 to 15 days) with minimal necrosis. When the aggregates reached the desired size, viable cell samples were harvested over periods of 3 to 4 days, and prepared for the following discussed analyses. Higher cell densities were observed with cocultured carcinoma cells than with the carcinoma cells cultured alone. Under the microgravity conditions, the carcinoma and normal cells were observed to express morphological and biochemical characteristics found in carcinoma cells in situ, and achieved three-dimensional cellular aggregates of up to 5 mm in diameter.

The assessment of fidelity of the carcinoma cell aggregates was based upon the regulation of specific oncogene markers and protein markers. The assessment of fidelity relates to the in situ environment. Morphological and biochemical characteristics of the aggregates were observed using scanning electron microscopy and histology. Samples from RWV cultures were taken at multiple time points throughout the course of the culturing procedures for histologic analysis (approximately 72 hours post inoculation and then every 72 hours). Standard immunostaining procedures, including antibodies specific to vimentin, keratin, and cytokeratin, were also utilized to evaluate differentiation and the presence of cellular components.

Two basic stains were performed on 20, 10, and 6-$\mu$m aggregate sample sections: hematoxylin and eosin (H&E)

and mucicarmine staining. After removal from the reactor vessels, samples were washed once with calcium-and magnesium-free PBS. The samples were suspended in a buffer containing 3% glutaraldehyde and 2% paraformaldehyde in 0.1M cacodylate buffer at pH 7.4. Samples of the cocultured prostate carcinoma cell aggregates and the monocultured prostate cell aggregates were analyzed by standard histology and electron microscopy techniques (Histologic Staining Methods, Armed Forces Institute of Pathology, American Registry of Pathology, 3rd.ed. New York, London, 1968).

Mucicarmine staining was performed according to the procedure of Sheehan and Hrapchak (Theory and Practice of Histotechnology, 2nd.ed, St. Louis, 1980). Tissues were fixed as previously stated. The samples were embedded in paraffin, blocked, and cut in multiple thicknesses. Sections were then mounted on slides and deparaffinized. The preparations were stained with Weigert's iron hematoxylin working solution for 5 minutes, then rinsed with running tap water for 5 minutes and placed in mucicarmine working solution for 30 minutes at room temperature. Slides were then rinsed with deionized water, stained with tartrazine solution for 1 to 5 seconds, then rinsed again with deionized water. The slides were dehydrated with zylene and mounted for analysis.

Results of staining showed the cocultured and cultured prostate carcinoma cell aggregates to exhibit intact cell subpopulations of differentiated and undifferentiated cells. Cellular structures, such as microvilli, were observed. The cellular protein, proteoglycan, was specifically identified in the cells of the three-dimensional aggregates. Protein markers, Prostate Specific Antigen (PSA) and Prostatic Acid Phosphatase (PAP), were observed in the prostate carcinoma cell aggregates.

Samples from the RWV cultures were taken for scanning electron microscopy at the same time as those taken for histological analysis. After removal from the reactor vessels, samples were washed once with CMF-PBS. The samples were fixed as previously stated. The samples were then placed in room temperature cacodylate buffer and postfixed according to the standard procedures described. Each sample was then placed in a modified BEEM capsule (SPI, West Chester, N.Y.). (The capsules were modified by removing the caps from two capsules, discarding the extra capsule, and slicing the conical ends off of the remaining capsule with a scalpel. A hole was then punched in each cap. A 4 cm$^2$ square of 50 $\mu$m polyester mesh (Tetko, Inc., Briarcliff, N.Y.) was placed over one open end of the capsule and a hole-punched cap attached to the end.) Once the sample was placed in the modified capsule, a 4 cm$^2$ of 50 $\mu$m polyester mesh was placed over the remaining open end and a hole-punched cap attached. Each capsule was then placed in a 50 ml tube and approximately 10 ml 1% osmium tetroxide (Electron Microscopy Sciences, Fort Washington, Pa.) added to each tube. The samples were allowed to fix for 45–60 minutes with the tube covered with aluminum foil. Samples were then rinsed thoroughly with Milli-Q ultrapure water (Millipore Corp., Bedford, Mass.). Filtered 1% solution of thiocarbohydrazide (TCH) (Electron Microscopy Sciences) was then added at approximately 10 ml to each tube and allowed to fix for 10 minutes with the tube covered with aluminum foil. The samples were then washed for 5 minutes with Milli-Q five times and fixed with 10 ml 1% buffered osmium tetroxide for 10 minutes while swirling the tube covered with aluminum foil. Samples were then rinsed with Milli-Q four times for 5 minutes each time, and dehydrated with increasing concentrations of EtOH as follows: 20% for 5 minutes; 50% for 5 minutes; 75% for 5 minutes; 95% for 5 minutes; 100% twice for 5 minutes each time.

Samples were dried by dehydration with hexamethyldisilazane (HMDS) (Electron Microscopy Sciences). After transfer to HMDS, samples were allowed to soak for 10 minutes, drained, and air dried overnight. Dried samples were sprinkled with a thin layer of silver paint on a specimen stub, dried, coated by vacuum evaporation with platinum-palladium alloy, and then examined in a scanning electron microscope at an accelerating voltage of 5 to 10 kV.

Micrographs taken of 3 to 5 day cultures showed substantial coverage of the microcarriers by three-dimensional prostate carcinoma cell aggregates. Microcarriers were uniformly covered with cell aggregates by 11 to 15 days of culturing in the vessel.

A cDNA library created from cocultured prostate carcinoma cells cultured in T-flasks and a cDNA library created from cocultured prostate carcinoma cells cultured in a rotating wall vessel were used in a subtractive hybridization process to identify mRNA of specific expressions associated with the particular culture environment. Oncogenic markers known to be specific for the cell types studied were analyzed by the method of Pardee and Lang for isolation of mRNA. The subtractive hybridization process used to create the cDNA libraries is a standard, commercially available technology (Invitrogen). A C-has/bas-1 probe was used to assess specific mRNA expression.

By separation of mRNA and DNA, basic patterns of isoenzymes were observed and determined to be stable. Protein markers, PSA and PAP, which are specific markers for prostate tumors, were expressed. Stable ploidy was also demonstrated. The oncogene markers and protein markers form a basis for assessing fidelity and comparing transitions from models grown in T-flasks to the high-fidelity three-dimensional cultures grown as cocultures and monocultures in the RWV.

A cDNA library was also created for the monocultured cell aggregates cultured in T-flasks and a library created for monocultured cells cultured in the rotating wall vessel using the same technology described for the cocultured cell culture cDNA libraries. Similar results at the cellular and molecular level were observed.

The assessment of carcinoma cell aggregate fidelity may also be based upon the ability of the aggregates to withstand successful transplantation into nude mouse models. The cocultured and monocultured prostate carcinoma cell aggregates will provide high-fidelity three-dimensional prostate carcinoma masses providing tumor models that closely resemble the carcinoma in situ.

Standard surgical transplantation procedures may be used to transfer cellular samples of the three-dimensional cocultured carcinoma cell aggregates to a nude mouse using standard surgical transplantation procedures. The transplants can be observed in parallel with controlled transplants of T-flask grown cocultured carcinoma cell aggregates.

It has been observed elsewhere that controlled transplants of cocultured carcinoma cells grown in T-flasks do not achieve successful transplantations into nude mice. It is predicted that the cocultured cell aggregates grown in the rotating culture vessel, however, will continue to develop and grow into larger tumors following transplantation into the nude mouse. The success of cell aggregate transplantation and evidence of continued tumor growth in the mouse will further demonstrate the high-fidelity characteristic of the cocultured three-dimensional prostate carcinoma cell aggregates.

Similarly, transplants of the prostate carcinoma cell aggregates grown in the RWV without the presence of normal cells may be transferred to a nude mouse and observed in parallel with controlled transplants of T-flask grown cocultured carcinoma cell aggregates. The ability of cell aggregates to transfer successfully into the mouse models will be indicative of the high-fidelity characteristic of the three-dimensional cell aggregates cultured in the rotating wall vessel.

Artificially-produced human bladder carcinomas were also propagated from carcinoma cells obtained from a human bladder carcinoma. The bladder carcinoma cell line propagated, designated T-24 by convention, is a primarily undifferentiated human bladder carcinoma cell line. The T-24 cell line is a mixed-bed carcinoma having a mixture of standard T-24 cell subpopulations. The bladder carcinoma cells were obtained from ATCC no. HTB 4. In the preferred embodiment of the inventive process, carcinoma cells were cocultured with normal human cells. The normal human cells were normal human bladder fibroblasts established from primary cultures from the normal bladders of organ donors. The normal human bladder fibroblast cell line was also obtained from Clonetics.

The same procedures and techniques described herein with reference to the culturing of human prostate carcinoma cells were followed to prepare high-fidelity three-dimensional human bladder carcinoma cell aggregates resembling carcinomas found in situ. Bladder carcinoma cells were cocultured or monocultured as described. Following culturing, the bladder carcinoma cell aggregates were analyzed as described above for prostate carcinomas. Similar characteristics of intact cell subpopulations of differentiated and undifferentiated cells, stable isoenzyme patterns, stable ploidy, stable and broad-based cell growth patterns and high-fidelity expression of specific cellular proteins, specifically proteoglycan, were observed with the bladder carcinoma cell aggregates as with the prostate carcinoma cells. The cocultured and monocultured human bladder carcinoma cell aggregates were found to be high-fidelity three-dimensional bladder carcinoma masses that provide tumor models that closely resemble the bladder carcinoma in situ.

Figure 2:
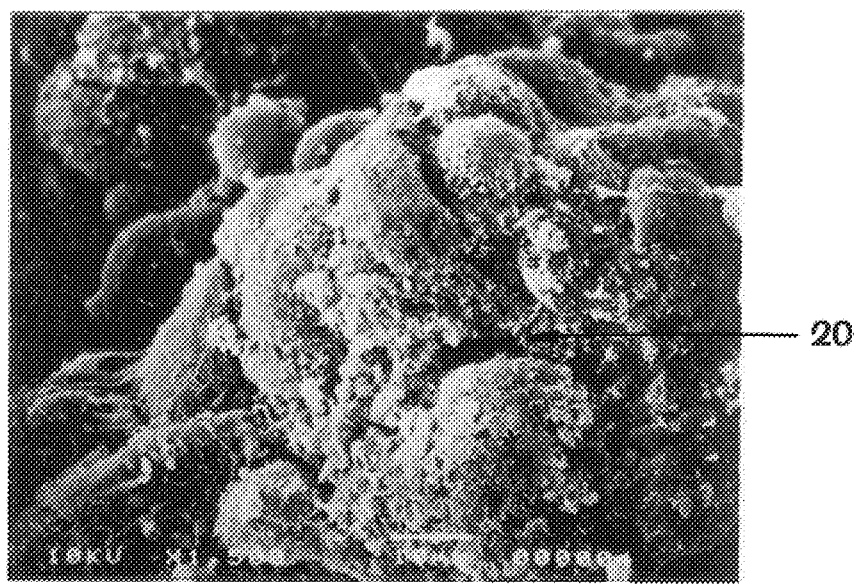
FIG. 2 is an SEM of the cells in FIG. 1 at 1500× magnification.

Scanning electron microscopy (SEM) views of T-24 bladder carcinoma cells monocultured and grown on microcarrier beads in the RWV are shown in FIGS. 1–6. (The kV reference on the Figures pertain to the voltage of the SEM. The SEM sequence number and magnification powers are also present in the Figures.) FIG. 1 is an SEM of a cultured high-fidelity three-dimensional bladder carcinoma cell aggregation at 350× magnification after 91 hours of culturing in the vessel in microgravity conditions. Confluent microcarriers and aggregate formation are seen. Individual cells generally indicated at reference numeral 10 can be distinguished. The three-dimensional aggregates are forming intact cell subpopulations of differentiated and undifferentiated cells. The size of the carcinoma cells and aggregates can be determined by the scale bar present on each Figure. The scale bar in FIG. 1 provides a measure of 50 $\mu$m. FIG. 2 is an SEM of the cells in FIG. 1 at 1500× magnification at 91 h. The greater magnification produces a "fuzzy" appearance of the cells, due to the microvilli of the cells at 20. The scale bar in FIG. 2 provides a measure of 10 $\mu$m.

Figure 3:
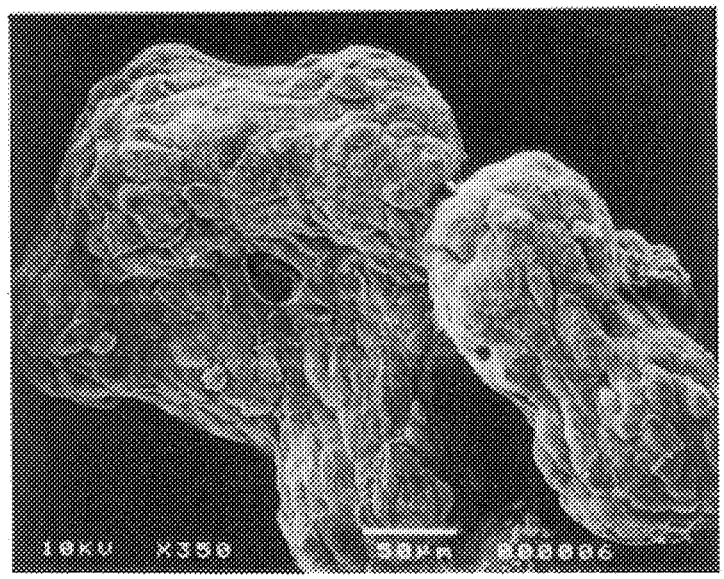
FIG. 3 is an SEM at 381 hours of a cultured high-fidelity three-dimensional bladder carcinoma cell aggregation at 350× magnification.
Figure 4:
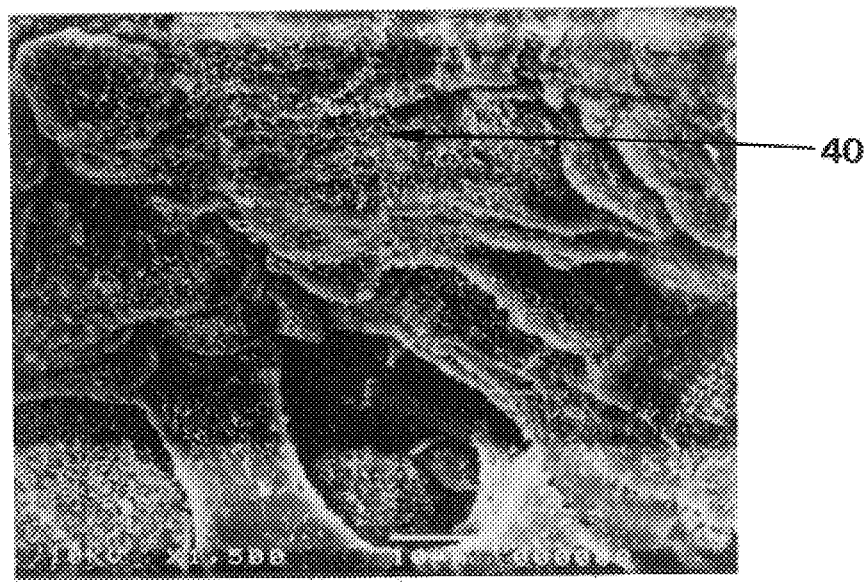
FIG. 4 is an SEM of the cells of FIG. 3 at 1500× magnification.
Figure 5:
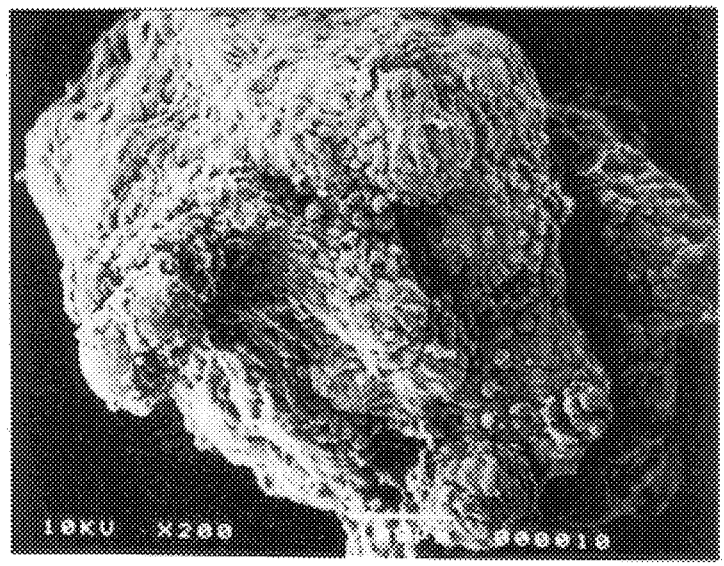
FIG. 5 is an SEM at 570 hours of cultured high-fidelity three-dimensional bladder carcinoma cell aggregates at 200× magnification.
Figure 6:
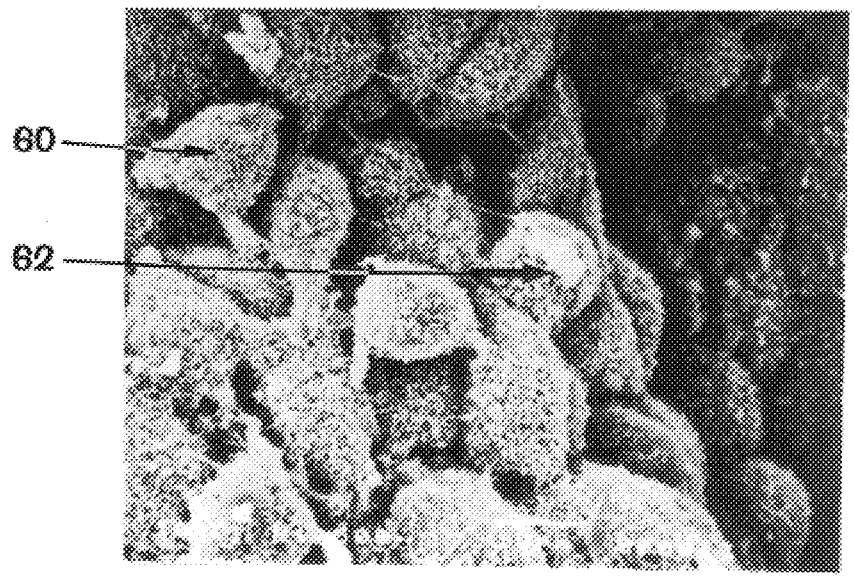
FIG. 6 is an SEM of the cells of FIG. 5 at 1500× magnification.

FIG. 3 is an SEM of a cultured high-fidelity three-dimensional bladder carcinoma cell aggregation at 350× magnification after 381 hours of culturing. Enhanced aggregate formation and cell growth can be seen. Cell growth is stable and broad-based growth patterns are demonstrated. The scale bar in FIG. 3 provides a measure of 50 $\mu$m. FIG. 4 is an SEM of the cells of FIG. 3 at 1500× magnification at 381 h. Extensive microvilli development 40 at the surface of the cells is evident. The scale bar in FIG. 4 provides a measure of 10 $\mu$m. FIG. 5 is an SEM of cultured high-fidelity three-dimensional bladder carcinoma cell aggregates at 200× magnification after 570 hours of culturing. The scale bar in FIG. 5 provides a measure of 100 $\mu$m. FIG. 6 is an SEM of the cells of FIG. 5 at 1500× magnification. Complete confluence and carcinoma cell aggregate formation is evident. Enhanced microvilli formation 60 and proteoglycan secretion 62 (at arrowhead) are apparent. The cells are expressing morphologic and biochemical characteristics found in carcinoma cells in situ. The scale bar in FIG. 6 provides a measure of 10 $\mu$m.

The examples included are not intended to limit the scope of the present invention. Human urogenital tract carcinoma cells have been cocultured with normal urogenital tract cells to produce aggregates of cells of high-fidelity three-dimensional carcinoma masses. Human urogenital tract carcinoma cells have also been monocultured to produce high-fidelity three-dimensional carcinoma masses. Other substitutions, modifications and variations are apparent to those skilled in the art without departing from the disclosure and scope of the invention.

What we claim is:

1. A process for producing aggregates of urogenital tract carcinoma cells comprising the steps of
   (a) inoculating urogenital tract carcinoma cells into a culture vessel containing culture media and a culture matrix;
   (b) culturing the urogenital tract carcinoma cells under microgravity conditions whereby the urogenital tract carcinoma cells form aggregates; and
   (c) maintaining the microgravity culture conditions whereby high-fidelity, three-dimensional urogenital tract carcinoma growth is achieved.

2. The process for producing aggregates of urogenital tract carcinoma cells of claim 1, wherein the carcinoma cells are a mixture of carcinoma cell subpopulations selected from the group consisting of prostate carcinoma, bladder carcinoma, and kidney carcinoma.

3. The process for producing aggregates of urogenital tract carcinoma cells of claim 1, wherein the culture media comprises fetal bovine serum and a tri-sugar based medium.

4. A process for producing aggregates of urogenital tract carcinoma cells of claim 3 wherein the tri-sugar based medium includes mixtures of the group consisting of fructose, galactose and glucose.

5. The process for producing aggregates of urogenital tract carcinoma cells of claim 1, wherein the microgravity culture conditions are created by the culture vessel.

6. The aggregates of urogenital tract carcinoma cells produced by the process of claim 5.

7. The process for producing aggregates of urogenital tract carcinoma cells of claim 1, wherein microgravity culture conditions are simulated.

8. The process for producing aggregates of urogenital tract carcinoma cells of claim 1, wherein the urogenital tract carcinoma cells are selected from the group consisting of prostate carcinoma, bladder carcinoma, and kidney carcinoma.

9. The process for producing aggregates of urogenital tract carcinoma cells of claim 1, wherein the microgravity culture conditions are created by having a horizontally rotating culture vessel in unit gravity producing the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel.

10. The aggregates of urogenital tract carcinoma cells produced by the process of claim 9.

11. The aggregates of urogenital tract carcinoma cells produced by the process of claim 1.

12. A process for producing aggregates of urogenital tract carcinoma cells comprising the steps of
   (a) inoculating normal mammalian cells into a culture vessel containing culture media and a culture matrix;
   (b) inoculating urogenital tract carcinoma cells into the culture vessel;
   (c) co-culturing the normal mammalian cells and the urogenital tract carcinoma cells under microgravity conditions; and
   (d) maintaining the microgravity culture conditions whereby high-fidelity, three-dimensional urogenital tract carcinoma growth is achieved.

13. The process for producing aggregates of urogenital tract carcinoma cells of claim 12, wherein step (a) further comprises culturing the normal mammalian cells under microgravity conditions whereby the normal mammalian cells form aggregates.

14. The process for producing aggregates of urogenital tract carcinoma cells of claim 12, wherein the normal mammalian cells are fibroblasts.

15. The process for producing aggregates of urogenital tract carcinoma cells of claim 12, wherein the normal mammalian cells are mesenchymal cells.

16. The process for producing aggregates of urogenital tract carcinoma cells of claim 12, wherein the urogenital tract carcinoma cells are selected from the group consisting of prostate carcinoma, bladder carcinoma, and kidney carcinoma.

17. The process for producing aggregates of urogenital tract carcinoma cells of claim 12, wherein the urogenital tract carcinoma cells are a mixture of carcinoma cell subpopulations.

18. The process for producing aggregates of urogenital tract carcinoma cells of claim 12, wherein the culture media comprises fetal bovine serum and a tri-sugar based medium.

19. A process for producing aggregates of urogenital tract carcinoma cells of claim 18 wherein the tri-sugar based medium includes mixtures of the group consisting of fructose, galactose and glucose.

20. The process for producing aggregates of urogenital tract carcinoma cells of claim 12, wherein the microgravity culture conditions are created by the culture vessel.

21. The aggregates of urogenital tract carcinoma cells produced by the process of claim 20.

22. The process for producing aggregates of urogenital tract carcinoma cells of claim 12, wherein the microgravity culture conditions are created by simulating microgravity.

23. A process for producing aggregates of urogenital tract carcinoma cells of claim 12, wherein the microgravity culture conditions are created by having a horizontally rotating culture vessel in unit gravity producing the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel.

24. The aggregates of urogenital tract carcinoma cells produced by the process of claim 23.

25. The aggregates of urogenital tract carcinoma cells produced by the process of claim 12.

* * * * *